United States Patent
Olalde Rangel

(10) Patent No.: US 7,416,748 B2
(45) Date of Patent: Aug. 26, 2008

(54) ARTHRITIS PHYTO-NUTRACEUTICAL SYNERGISTIC COMPOSITION

(75) Inventor: Jose Angel Olalde Rangel, Clearwater, FL (US)

(73) Assignee: Jose Angel Olade Rangel, Clearwater, FL (US)

( * ) Notice: Subject to any disclaimer, the term of this patent is extended or adjusted under 35 U.S.C. 154(b) by 96 days.

(21) Appl. No.: 11/462,218

(22) Filed: Aug. 3, 2006

(65) Prior Publication Data

US 2008/0044496 A1    Feb. 21, 2008

(51) Int. Cl.
*A61K 31/76* (2006.01)
*A61K 36/258* (2006.01)
*A61K 36/906* (2006.01)
*A61K 36/48* (2006.01)
*A61K 36/81* (2006.01)
*A61K 36/00* (2006.01)
*A61K 31/70* (2006.01)
*A23L 1/216* (2006.01)

(52) U.S. Cl. .................. 424/728; 424/775; 424/773; 424/756; 424/779; 424/757; 424/760; 424/777; 426/637; 514/62

(58) Field of Classification Search .................. None
See application file for complete search history.

*Primary Examiner*—Christopher R. Tate
*Assistant Examiner*—Catheryne Chen

(57) ABSTRACT

A Phytoceutical composition for the prevention and treatment of arthritis is provided. A specific combination of extracts of plants and nutraceuticals is taught, as well as principles for varying the formulations based on categorizing plants and nutraceuticals into one of three groups, Energy, Bio-Intelligence, and Organization and selecting several plants and nutraceuticals from each group. Such combinations have synergistic effects, with minimal side effects.

1 Claim, No Drawings

ARTHRITIS PHYTO-NUTRACEUTICAL SYNERGISTIC COMPOSITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phytoceutical formulation used to treat arthritis diseases. The formulation is a particular combination of plants that have synergistic effect and nutraceuticals. Principles for selecting beneficial formulations are provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process. As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines.

This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). Conclusion: On one hand, synthetics may have the required efficacy for disease treatment; however this can be marred by severe side effects. On the other hand, despite the excellent medicinal qualities of many plants, they are individually insufficient to take chronic degenerative diseases into remission. However, there is mounting evidence which demonstrates that medical plants contain synergistic efficacy and/or side-effect neutralizing combinations (Gilani and Rahman, 2005). Thus, what is needed in the art are better treatment regimes with improved patient tolerance, while providing sufficient efficacy.

SUMMARY OF THE INVENTION

A number of known beneficial plants and tonics were classified according to their capacity to enhance the three main elements that support overall health: Energy (E), Bio-intelligence (I) and Organization (O). A synergistic effect is expected when all three categories of herbs (E, I, O) are included in a formulation, preferably at least two or three or four plants from each category. Thus, one embodiment of the invention provides a method of selecting the disease treating formulation according to these principles. An example of a formulation prepared this way is provided and additional formulations are being prepared and tested.

Another embodiment of the invention provides an effective, natural composition for treating arthritis and its symptoms. The composition can be used alone, or can be combined with simultaneous use of one or more pharmaceutical compositions. It can be used for the treatment of arthritis, rheumatoid arthritis and osteoarthritis as well as any inflammatory condition of the joints and their symptoms, pain swelling, heat, redness and limitation of movement.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.5, 2, 5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only and should not serve to unduly limit the invention.

EXAMPLE 1

Plant Characteristics—Arthritis Disorders

Energy Supplying Phytoceuticals

*Ajuga turkestanica* Its main active principle turkesterone, a phytoecdysteroid possessing an 11alpha-hydroxyl group. Ecdysteroids normalize NADH dehydrogenase activity, enzyme which catalyzes electron transfer from NADH to ubiquinones in the oxidative phosphorylation processes which occur at the mitochondrial level, contributing to the potential electrochemical buildup required to produce ATP. It also normalizes the succinate dehydrogenase enzyme which participates in the tricarboxilic acid cycle, which translates to ATP synthesis and patient energy level increases [Tashmukhamedova M A, Almatov K T, Syrov V N. Comparative study of the effect of ecdysterone, turkesterone and nerobol on the function of rat liver mitochondria in experimental diabetes. Vopr Med Khim. 1986; 32:24-8].

*Panax quinquefolius* (American Ginseng, Anchi, Canadian Ginseng, Five Fingers, Ginseng, American, North American Ginseng, Red Berry, Ren Shen, and Tienchi) main active components are ginsenosides (protopanaxadiols and protopanaxatriols types). These substances confer energizing properties because they increase ATP synthesis. Also, they may produce a variety of beneficial effects: anti-inflammatory, immune stimulating (inespecific humoral and cellular), and antioxidant effects. Results of clinical research studies demonstrate *Panax quinquefolius*' immune-modulating activity; improves physical and mental performance and increases resistance to exogenous stress factors. Its phytosterols inhibit prostaglandin synthesis (this partly explains its anti-inflammatory activity). The incorporation of this phytomedicine provides at least 86 active principles in a single therapeutic.

*Rhodiola rosea* (Golden Root, Roseroot) consists mainly of phenylpropanoids (rosavin, rosin, rosarin (specific to *R. rosea*), phenylethanol derivatives (salidroside, rhodioloside, tyrosol), flavanoids (catechins, proanthocyanidines, rodiolin, rodionin, rodiosin, acetylrodalgin, tricin), monoterpenes (rosiridol, rosaridin), triterpenes (daucosterol, beta-sitosterol), and phenolic acids (chlorogenic and hydroxycinnamic, gallic acids). It also contains organic acids (gallic, caffeic, and chlorogenic acids) and p-Tyrosol. There are many species of *Rhodiola*, but it appears that the rosavins are unique to *R. Rosea*, and it is the preferred species. It is an energizer because it activates the synthesis or resynthesis of ATP in mitochondria and stimulates reparative energy processes after intense exercise. Incorporation of this phytomedicine provides at least 20 active principles in a single therapeutic.

Bio-Intelligence Modulators

*Glycyrrhiza glabra* (Commom Licorice, Licorice, Licorice-Root, Smooth Licorice) consists mainly of Saponoside: glicirricin, 24-OH-glicirricin, glabranines A and B, glicirretol, glabrolide, isoglabrolide. Flavonoids: flavanones (liquiritigenin, liquiritin), chalcones (isoliquiritin, isoliquiritigenin), glabrol, isoflavonoids (neoliquiritin, hispaglabridines). Triterpenes, sterols. Polisaccarides (glicirrizan GA), starch, glucose and sacarose. Also glicirricinic, glycyrrhizin, glycyrrhetinic and glicirricic acids. Of this active principles, glycyrrhizin and glycyrrhetinic acid have shown antiinflammatory activity by inhibition of 11 beta-hydroxysteroid dehydrogenase, an enzyme related to corticosteroid metabolism (Homma M, Oka K, Niitsuma T, Itoh H. A novel 11 beta-hydroxysteroid dehydrogenase inhibitor contained in sai-boku-to, an herbal remedy for steroid-dependent bronchial asthma. J Pharm Pharmacol. 1994; 46:305-9). Also, *Glycyrrhiza glabra* can suppress in cell-free systems the activities of 5-lipoxygenase (5-LO) and cyclooxygenase-2 (COX-2), key enzymes in the formation of proinflammatory eicosanoids from arachidonic acid (Herold A, Cremer L, Calugaru A. Hydroalcoholic plant extracts with anti-inflammatory activity Roum Arch Microbiol Immunol. 2003; 62:117-29). *G. glabra* provides 314 active principles in a single therapeutic.

*Morinda citrifolia* (Noni, Indian Mulberry, Ba Ji Tian, Nono, Nonu, Fruta de Queso and Nhau) A large range of its components have been identified. Noni encompasses at least 23 active principles, 5 vitamins and 3 minerals. Among them: several acids, vitamins (A & C), potassium, Nordamnacanthal and Morindone, anthraquinones, fitosterols, flavonolglicosides, aucubine, alizarine and others. In the range of therapeutic activities are included: 1) Immune-stimulant: The fruit's extracts stimulate the release of various interleukins, including interleukine-1beta, IL-10, IL-12 and interferon-gamma. Proceedings of the 7th Annual Conference Eicosanoids and other bioactive lipids in cancer, inflammation and related disease (2001, Nashville, Tenn.) publishes *Morinda's* anti-inflammatory properties—greater than Celecoxib—to selectively inhibit COX2. 2). Anti-inflammatory effect: The fruit's extracts inhibits tumor necrosis factor-alpha, an important mediator of the inflammation process. Its anti-inflammatory activity is also explained by its strong antioxidant properties, scavenging free radicals and diminishing lipid peroxidation. One study compared Noni with three known anti-oxidants: Vitamin C, grape seed powder and picnogenol, offering greater capacity to scavenge free radicals (2.8, 1.1, and 1.4 respectively). This plant provides at least 31 active principles in a single therapeutic.

*Uncaria tomentosa* (Cat's Claw, Peruvian Cat's Claw, Samento, Saventaro, Uña de Gato, also *Uncaria guianensis*) has several alkaloids including pentacyclic oxindole alkaloids (POA) (isomitraphylline, isopteropodine, mitraphylline, pteropodine, speciophylline, uncarine F), tetracyclic oxindol alkaloids (TOA) (isorynchophylline, rynchophylline), glycosides (triterpenic quinovic acid glycosides), hirsutine, tannins, catechins, phytosterols (beta-sitosterol, campesterol, stigmasterol), triterpenes, polyphenols, flavanols and oligomeric proanthocyanidines (OPC). It is an immune-stimulant, anti-inflammatory and antioxidant. The Immune-stimulant property is attributed to pentacyclic oxindoles, with isopteropodine being the most effective. The immunologic activity includes the liberation of an endothelial factor which induces the proliferation of granulocytes (neutrophils and monocytes) and lymphocytes T and B; increases the rate of phagocytes and increases the production of interleukins (IL-1 and IL-6), and also suppresses the necrosis kappa factor (NF-k). The Anti-Inflammatory activity includes: inhibition of the synthesis of necrosis tumor alpha factor (TNF—) which is associated with the inflammation process; reduction of the production of prostaglandins ($PGE_2$) and reduction of the nitric oxide synthesis, which makes it an ideal treatment for inflammatory arthropathies. Its efficiency is 15% superior to indometacine. The Antioxidant activity is attributed to polyphenols and triterpenes that capture and eliminate free radicals, protecting the cellular membranes. This phytomedicine provides at least 10 active ingredients.

Organizational Improvers

*Capsicum frutescens* (Cayenne, Chili, Hot Pepper, Red Chili, Spur Pepper, Tabasco). Its main active principles are Capsaicinoides (capsaicin, dihydrocapsaicin, nordihydrocapsaicin, homocapsaicin, and homodihydrocapsaicin), capsantin, capsorubin, flavonoides (apioside and lutein), essential oils, vitamin C, vitamin B1, vitamin B2, Fe and Cu. The active principles which explain its anti-inflammatory properties are: 1,8-cineole, alpha-linolenic-acid, ascorbic-acid, caffeic-acid, capsaicin and caryophyllene, which act as antioxidants, scavenging free radicals and reducing lipid peroxidation in cellular membranes (Howard L R, Talcott S T, Brenes C H, Changes in phytochemical and antioxidant activity of selected pepper cultivars—*Capsicum* species—as influenced by maturity. J Agric Food Chem. 2000; 48:1713-20). Incorporation of *C. frutescens* provides at least 195 active principles in a single therapeutic.

Chondroitin sulfate: In a similar manner to Glucosamine sulfate, Chondroitin sulfate provides essential additional substrata for the formation of a healthy articular matrix. The scientific evidence corroborates that the oral administration of chondroitin sulfate in articular disease cases, reduce the symptoms and non-steroid anti-inflammatory requirements. The incorporation of this phytomedicine provides 1 active principle.

*Curcuma longa* (Indian Zafran, Azafrán de la India, turmeric, Kurkuma, Safran des Indes, yellow root). Its main active principles are carbohydrates, essential oils, fatty acids, curcuminoids (curcumin, demethoxil curcumin, and bidemethoxil curcumin) and other polypeptides such as turmerine. Curcumin (diferuloylmethane) and turmerine are the compounds responsible for its biological activity, of great utility in articular inflammatory processes.

Laboratory studies have identified a number of different molecules involved in inflammation that are inhibited by curcumin including phospholipase, lipooxygenase, cyclooxygenase 2, leukotrienes, thromboxane, prostaglandins, nitric oxide, collagenase, elastase, hyaluronidase, monocyte chemoattractant protein-1 (MCP-1), interferon-inducible protein, tumor necrosis factor (TNF), and interleukin-12 (IL-12). Curcumin ha demonstrated to be safe in—at least—six human trials and has anti-inflammatory activity (Chainani-Wu N. Safety and anti-inflammatory activity of curcumin: a component of tumeric—*Curcuma longa*. J Altern Complement Med. 2003; 9: 161-8). Incorporation of *C. longa* provides at least 89 active principles.

*Dioscorea villosa* (Mexican wild yarn, china root, colic root, rheumatism root, huesos del diablo, yuma.) Steroid sapogenins are the main active principles, among which are dioscine, dioscorine and diosgenine. *Dioscorea* also contains salts and minerals, such as: aluminum, calcium, chrome, cobalt, iron, selenium, silica, sodium, tin, zinc, magnesium, manganese, phosphorus and potassium. It also has vitamins (ascorbic acid), beta-carotene, niacine, riboflavine y thiamine. The active principles which explain its antioxidant and anti-inflammatory properties are diosgenine, ascorbic-acid and magnesium. Liagre et al show that diosgenine induces apoptosis in human rheumatoid arthritis synoviocytes and regulates the cyclooxygenase-2 overexpression correlated with overproduction of endogenous prostaglandin E2. (Liagre B, Vergne-Salle P, Corbiere C. *Diosgenin*, a plant steroid, induces apoptosis in human rheumatoid arthritis synoviocytes with cyclooxygenase-2 overexpression. Arthritis Res Ther. 2004; 6:373-83). The incorporation of this phytomedicine provides at least 29 active principles in a single therapeutic.

Glucosamine sulfate The effect of glucosamine sulfate in the detention or slowing articular degeneration seems to be its ability to act as an essential substratum and stimulate the synthesis of glucosaminoglicans as well as the hyaluronic acid structure necessary for the formation of proteoglicans found in the articulations structural matrix. The incorporation of this phytomedicine provides 1 active principle.

*Harpagophytum procumbens* (Devil's Claw, Uña del Diablo, Grapple Plant). The main active principles which explain the plant's anti-inflammatory properties are: harpagosides, harpagine, procumbides, procumbosides, and fitosterols such as beta-sitosterol and stigmasterol.

The anti-inflammatory actions of *Harpagophytum procumbens* is due to its action on eicosanoid biosynthesis: harpagosides inhibited lipo-polysaccharide-induced mRNA levels and protein expression of cyclooxygenase-2 and inducible nitric oxide. These inhibitions appeared to correlate with the suppression of NF-kappaB activation by harpagoside. Another study demonstrates that it inhibits the production of tumor necrosis factor alpha (TNF-alpha), related with the inflammatory process. They also diminish the inflammatory process, by inhibiting Cycloxigenase and Nitric Oxide Synthase, which leads to a reduction in the synthesis of the pro-inflammatory substances prostaglandin E2 (PGE2) and nitric oxide. Inflammatory cartilage diseases such as arthritis and osteoarthritis are characterized by a loss of articular cartilage due to an imbalance between synthesis and degradation of the extra cellular cartilage matrix. These diseases are accompanied by an increased induction of cytokines such as interleukin 1beta (IL-1beta) and tumor necrosis factor alpha (TNF-alpha). The increased release of cytokines leads to an enhanced production of matrix-degrading enzymes e.g. the matrix metalloproteinases (MMPs). *Harpagophytum* significantly decreased the production of MMPs (MMP-1, MMP-3, and MMP-9) in chondrocytes. The IL-1beta-induced production of MMPs was also significantly reduced. The capability of *Harpagophytum* to suppress the MMP—production via the inhibition of the synthesis of inflammatory cytokines could explain its therapeutic effect in arthritic inflammations. Similar studies demonstrate that *Harpagophytum* offers and anti-inflammatory action similar to synthetic selective COX2 inhibitor NSAID's. Incorporation of this phytomedicine provides at least 34 active principles in a single therapeutic.

*Tribulus terrestris* (Puncture-vine) The fruit and root of *Tribulus* contains active principles such as phytoesteroides, flavonoids, alcaloids y glucosides, steroidal saponines of the furostanol type, which produce anti-inflammatory effects. The inhibitors of prostaglandin biosynthesis and nitric oxide production have been considered as potential anti-inflammatory agents. Tribulus terrestris showed potent inhibition of COX-2 activity. (Hong C H, Hur S K, Oh O J. Evaluation of natural products on inhibition of inducible cyclooxygenase (COX-2) and nitric oxide synthase (iNOS) in cultured mouse macrophage cells. J Ethnopharmacol. 2002; 83:153-9). The incorporation of this phytomedicine provides 47 active principles in a single therapeutic.

EXAMPLE 2

Composition—Arthritis Disorders

A particularly preferred composition is shown in Table 1. Ratios reflect the concentration of active ingredient over the natural state, and the amounts provided are mg of extract. Obviously, the amount should be increased where the strength is reduced, and vice versa.

A particularly preferred composition is shown in Table 1.

TABLE 1

| Composition | | |
|---|---|---|
| Active Agent | Ratio | Amount (mg) |
| Energy enhancers | | |
| *Ajuga turkestanica* | 5:1 | 4 |
| *Panax quinquefolius* | 4:1 | 4 |
| *Rhodiola rosea* root extract | 10:1 | 16 |
| Bio-Intelligence modulators | | |
| *Glycyrrhiza glabra* | 10:1 | 4 |
| *Morinda citrifolia* fruit extract | 10:1 | 162 |
| *Uncaria tomentosa* inner bark extract | 10:1 | 162 |
| Organization improvers | | |
| *Capsicum frutescens* | 10:1 | 8 |
| Chondroitin sulfate | 1:1 | 162 |
| *Curcuma longa* | 10:1 | 16 |
| *Dioscorea villosa* | 10:1 | 16 |
| Glucosamine sulfate | 1:1 | 162 |
| *Harpagophytum procumbens* | 10:1 | 162 |
| *Tribulus terrestris* | 10:1 | 32 |
| Total | | 910 |

EXAMPLE 3

Clinical Study One

Effectiveness and Tolerance

A retrospective, descriptive, multicenter study was undertaken with 309 patients affected by Rheumatoid Arthritis and which were treated at the Adaptogenic Medical Centers during the period between October 2002, and October 2005, to determine the effectiveness of a phyto-nutraceuticals formulation based on Systemic Medicine. Of these patients, 81.6% corresponded to female gender. The groups' (both men and women) average age was 53 years. The patients had received a conventional therapy during a prolonged time, without the desired results. The phyto-nutraceuticals composition demonstrated improvement in morning rigidity (92.6% of the patients), pain (96.4% of all patients); improvement in inflammatory signs (94.4% of all cases) and improvement of the functional limitation in 94% of the patients. Tolerance to treatment was excellent: 98.7% of the cases. We can conclude that the formulation is an unexpectedly superior treatment, better than conventional therapeutic schemes, since it controlled the diseases' symptoms, improved the quality of life and does not produce adverse indirect effects, becoming an excellent treatment for rheumatoid arthritis.

EXAMPLE 4

Arthritis Clinical Study Two

Effectiveness and Tolerance

In order to evaluate the effectiveness of a phyto-nutraceuticals combination formulated under the principles of the Systemic Medicine, a prospective study with a group of 30 patients with knee osteoarthrosis was carried out. All patients received 10 daily 901 mg capsules, during a period of 3 months. 96.6% of the evaluated patients observed an improvement in pain, morning rigidity, rank of mobility, displacement, and degree of tumefaction as well as a significant diminution of concomitant therapy with analgesics. The tolerance to the product was excellent. This phyto-nutraceuticals formulation is an excellent alternative for the handling of Osteoarthritic patients with femoropatteral knee with chondromalacia and meniscopathy, guaranteeing a better quality of life.

EXAMPLE 5

Principles for Selecting Synergistic Combinations

In order to explain the range of formulations encompassed by the invention, we have categorized beneficial plants and nutraceuticals into one of three groups, each of which should be present for synergistic effect. The classifications are: Energy, Bio-Intelligence and Organization. Plants and nutraceuticals classified under Energy are associated with ATP synthesis (such as the Krebs cycle, oxidative phosphorylation, beta-oxidation, etc.). Plants and nutraceuticals classified under Bio-Intelligence are those that regulate the neuroendocrine and immunological systems and cellular processes, thus controlling the interactions between the various systems in the body. Finally, plants and nutraceuticals classified under Organization are those that relate to the structure and function of specific organs. Combinations of plants and nutraceuticals from these three classification groups have synergistic effect because they address each necessary component of cellular and organic health—in effect they provide the triangle on which healing is fully supported.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated *Hydnocarpus wightiana*). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000; 97:1433-7.

A further demonstration may be provided of synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E.g., Gohil, et al., mRNA Expression Profile of a Human Cancer Cell Line in Response to Ginkgo Biloba Extract: Induction of Antioxidant Response and the Golgi System, Free Radic Res. 2001; 33:831-849.

Finally there may be further presentation of gene expression results using whole-genome microarray analysis to demonstrate the formulation's capability to provide gene activation (upregulation or downregulation).

What is claimed is:

1. A method of treating arthritis comprising administering an effective amount of a composition comprising, 4 mg *Ajuga turkestanica*, 4 mg *Panax quinquefolius*, 16 mg *Rhodiola rosea* root extract, 4 mg *Glycyrrhiza glabra*, 162 mg *Morinda citrifolia* fruit extract, 162 mg *Uncaria tomentosa* inner bark extract, 8 mg *Capsicum frutescens*, 162 mg Chondroitin sulfate, 16 mg *Curcuma longa*, 16 mg *Dioscorea villosa*, 162 mg Glucosamine sulfate, 162 mg *Harpagophytum procumbens* and 32 mg *Tribulus terrestris*.

* * * * *